(12) United States Patent
Bolz

(10) Patent No.: US 7,052,596 B2
(45) Date of Patent: May 30, 2006

(54) LINEAR LAMBDA PROBE EVALUATION CIRCUIT

(75) Inventor: Stephan Bolz, Pfatter (DE)

(73) Assignee: Siemens Aktiengesellschaft, Munich (DE)

(*) Notice: Subject to any disclaimer, the term of this patent is extended or adjusted under 35 U.S.C. 154(b) by 520 days.

(21) Appl. No.: 10/320,209

(22) Filed: Dec. 16, 2002

(65) Prior Publication Data

US 2003/0101796 A1 Jun. 5, 2003

Related U.S. Application Data

(63) Continuation of application No. PCT/DE01/02165, filed on Jun. 11, 2001.

(30) Foreign Application Priority Data

Jun. 16, 2000 (DE) ............................... 100 29 794

(51) Int. Cl.
  *G01N 27/409* (2006.01)
  *G01N 27/41* (2006.01)
(52) U.S. Cl. .................. 205/784.5; 204/406; 204/425; 73/23.32
(58) Field of Classification Search ................ 204/406, 204/425, 426, 427; 205/784.5; 73/23.31, 73/23.32
See application file for complete search history.

(56) References Cited

U.S. PATENT DOCUMENTS

| 4,981,125 A | * | 1/1991 | Kato et al. .................. 123/693 |
| 5,173,167 A | | 12/1992 | Murase et al. |

FOREIGN PATENT DOCUMENTS

| DE | 43 04 966 A1 | 8/1994 |
| DE | 198 36 128 A1 | 2/2000 |
| EP | 0 973 029 A1 * | 1/1999 |
| EP | 1 001 261 A1 | 11/1999 |

OTHER PUBLICATIONS

Datasheet CJ110, Robert Bosch GMBH, "Integrated Circuit for Continuous Lambda Regulation," pp. 1-6, Sep. 1998.

* cited by examiner

*Primary Examiner*—Kaj K. Olsen
(74) *Attorney, Agent, or Firm*—Baker Botts L.L.P.

(57) ABSTRACT

The pumping current source (P) required for operating the linear lambda probe is wired in such a manner that its inverting input is connected to the third probe terminal (Vp+), its non-inverting input is connected to the potential of the mean voltage (VM), and that its output is connected to the second probe terminal (Vp-/Vs-).

15 Claims, 1 Drawing Sheet

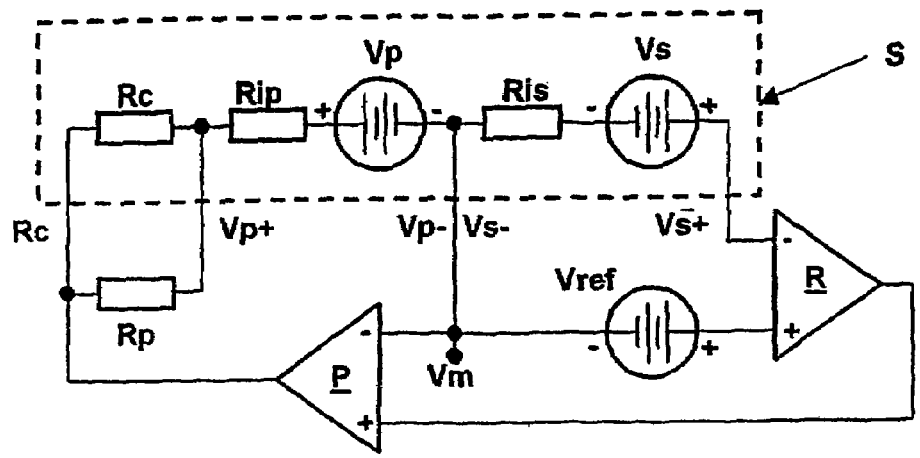
PRIOR ART  Fig 1
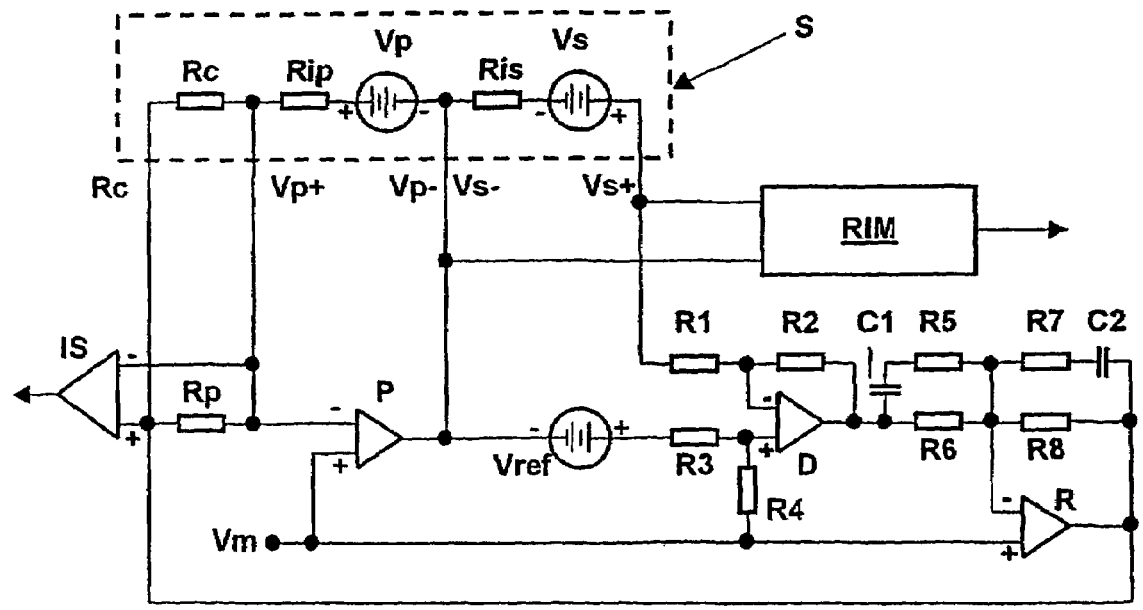
Fig 2

LINEAR LAMBDA PROBE EVALUATION CIRCUIT

CROSS REFERENCE TO RELATED APPLICATION

This application is a continuation of copending International Application No. PCT/DE01/02165 filed Jun. 11, 2001 which designates the United States, and claims priority to German application number 10029794.3 filed Jun. 16, 2000.

BACKGROUND OF THE INVENTION

The invention relates to a device for operating a linear lambda probe of an internal combustion engine.

Legislators are using tax incentives to promote the development of motor vehicles with increasingly low emissions of pollutants and fuel consumption. In spark ignition engines with stoichiometric mixture formation ($\lambda=1$), this has led to the development of SULEV vehicles (Super Ultra Low Emission Vehicles) with extremely low emissions.

In order to save fuel, engines with direct HPDI (High Pressure Direct Injection) fuel injection are currently being developed and launched onto the market. The fuel is injected directly into the combustion chamber here at an increased pressure (for example 150 bar). The preparation of the mixture which it makes possible can vary between rich, stoichiometric and lean. For the partial load mode of the engine, a lean mixture formation provides appreciable consumption advantages.

Both developments require a significantly more precise regulation of the mixture than is possible with the lambda probes (binary step-change probes) which are customary today. These probes have an extremely restrictive measuring range about $\lambda=1$ and are therefore unsuitable for measurements in the lean operating mode $\lambda>1$.

For this reason, lambda probes with an extended linear measuring range, which are referred to as linear lambda probes, are now being increasingly used.

Binary step-change probes have a pair of electrodes which are separated by a zircon ceramic, which acts as an electrolyte at high temperatures. One electrode is located in the exhaust gas stream here, and the other in air. When there is a different concentration of oxygen between the air and the exhaust gas, a voltage value which is determined by the Nernst diffusion equation is produced between the electrodes. Typical values of this voltage are approximately 200 mV in air, approximately 450 mV when $\lambda=1$ and approximately 800 mV in a rich mixture. In the region surrounding $\lambda=1$, the oxygen concentration changes by several powers of ten, which is manifested in a sudden change in the probe voltage in this region.

The linear lambda probe is of complex design. It has two pairs of electrodes and one measuring chamber which is connected to the exhaust gas stream via a diffusion barrier. The first pair of electrodes is arranged between the measuring chamber and air and is used—similarly to the step-change probe—to measure the oxygen concentration in the measuring chamber. The second pair of electrodes is arranged between the measuring chamber and the exhaust gas stream. When a current of a corresponding polarity is applied, said pair of electrodes permits oxygen ions to be pumped out of the measuring chamber or into it. Designation: pumping electrodes.

In this way it is possible to generate a dynamic equilibrium between the flow of oxygen through the diffusion barrier and the flow of oxygen ions through the pair of pumping electrodes. The oxygen concentration in the measuring cell which can be determined using the measuring electrodes is suitable as a control criterion here. A preferred value is, for example, 450 mV for $\lambda=1$. The pumping current Ip which flows in this case is therefore a measure of the oxygen concentration in the exhaust gas (and also of $\lambda$ after numerical conversion).

The relation between the oxygen concentration in the exhaust gas and the pumping current is influenced by several probe parameters. For fabrication reasons, the dynamic resistance of the diffusion barrier fluctuates somewhat. This would result in a deviation in the transformation ratio (amplification error). During fabrication this is compensated by measuring and inserting a calibrating resistor Rc into the probe plug.

The calibrating resistor permits the pumping current in the following evaluation circuit to be scaled, which again compensates the transformation ratio.

Furthermore, the dynamic resistance of the diffusion barrier has a temperature dependence, which in turn leads to errors in the transmission ratio. This is counteracted by measuring the probe temperature and controlling it by means of a heating element which is installed in the probe. For reasons of cost, a separate thermal element is dispensed with here. Instead, the highly temperature-dependent internal resistance of the probe is measured.

Hitherto, the application of the linear lambda probe was restricted to the noncharged, stoichiometric operation (Pa=1 bar, $\lambda=1$) of the engine. Correspondingly, only small pumping currents were also necessary to maintain the equilibrium ($\lambda=1$) in the measuring cell (|Ip|<~2.5 mA).

For lean engines, operation up to $\lambda=4$ is provided for, which requires a drastically increased pumping current. When operating in a supercharged engine (turbo), an exhaust gas pressure of up to 2 bar is obtained. The pressure sensitivity of the probe leads to a further increase in the maximum necessary pumping current to ±12 mA. This is possible only to a partial extent with evaluation circuits which are currently on the market.

A known evaluation circuit is illustrated in FIG. 1 and will be described in more detail below.

This circuit has certain disadvantages:

When the evaluation circuit is supplied with a supply voltage Vcc=5 V which is already generally present, a mid-voltage Vm of approximately 2.5 V is obtained. The voltage chain which is present at the probe is then:

$$Vm < |Rc^*Ip + Vp| + Vsat;$$

Rc=30 to 100$\Omega$=entire calibrating resistance (dependent on manufacturer),

Vp=−350 to +450 mV; polarization voltage of the pumping cell,

Vsat=100 to 200 mV; saturation voltage of the pumping current source P.

This limits the maximum possible pumping current Ip to <10 mA, and therefore does not correspond to the requirements (Ip=±12 mA).

Alternatively, a higher supply voltage of the circuit could be used, for example 8 V. However, this would have the disadvantage that an additional expensive voltage controller would be necessary and the circuit would no longer function when the battery voltage is low (<8.5 V). (the minimum acceptable battery voltage is defined as $Vbat_{min}=6$ V).

A common mode signal (Vm±2 V) is superimposed on the pumping current Ip. Due to the finite common mode suppression of real integrated amplifiers (for example 65 dB), the measurement is falsified by up to ±0.3%.

In addition, the polarization voltage of the pumping cell (−350 mV when λ<1) results in a zero point error ΔIp of approximately 5 μA. As the pumping current Ip is the primary measurement signal of the oxygen probe, these errors directly affect the overall precision of the probe measurement signal. This restricts the precision of the lambda control and thus constitutes a significant problem.

SUMMARY OF THE INVENTION

The object of the invention is to improve the known device for operating a linear lambda probe to the effect that values of the pumping current Ip which correspond to the requirements set are made available, that the common mode error which is described is avoided and the precision of the measurement is significantly improved, and that the probe is still operationally capable even when the battery voltage is low (Vb=+6 V).

This object may be achieved according to the invention by means of a device for operating a linear lambda probe of an internal combustion engine whose first terminal, second terminal, third terminal and fourth terminal are connected to an evaluation circuit which has a difference amplifier which forms the difference between the Nernst voltage measured in the lambda probe and a reference voltage related to a mid-voltage, and having a pumping current source which converts this difference into a pumping current which generates, at the standardizing resistor of the probe, a voltage which can be measured by means of a measuring amplifier and which is used as a measure of the oxygen concentration in the exhaust gas of the internal combustion engine, wherein the inverting input of the pumping current source is connected to the third probe terminal, the noninverting input of the pumping current source is connected to the potential of the mid-voltage, the output of the pumping current source is connected to the second probe terminal, in that the difference amplifier has connected downstream of it a controller whose inverting input is connected to the output of the difference amplifier, whose noninverting input is connected to the potential of the mid-voltage and whose output is connected to the fourth probe terminal, the noninverting input of the measuring amplifier is connected to the fourth probe terminal and to the output of the controller, and wherein the inverting input of the measuring amplifier is connected to the third probe terminal, the voltage which can be measured at the calibrating resistor being referred to the mid-voltage.

The controller may be an integral-action controller, a proportional-plus-derivative controller, or a proportional-plus-integral-plus-derivative controller.

Another embodiment according to the present invention is a device for operating a linear lambda probe having a first, second, third, and fourth terminal, which comprises a differential amplifier having an inverting input being coupled with the first terminal and a noninverting input being coupled in series with a reference voltage source and the second terminal and having an output, a controller having an inverting input coupled with the output of the differential amplifier and a noninverting input receiving a mid voltage and an output, a pumping current source having an inverting input coupled with the third terminal and a noninverting input receiving the mid voltage and an output coupled with the second terminal, and an amplifier having an inverting input coupled with the second terminal and a noninverting input coupled with the first terminal and the output of the controller.

The reference source may be coupled with the mid voltage. The controller can be an integral-action controller, a proportional-plus-derivative controller, or a proportional-plus-integral-plus-derivative controller. The pumping current source and the controller each may comprise an operational amplifier. The differential amplifier further can comprise a first resistor coupled between the inverting input and the output, a second resistor coupled between the inverting input and the first terminal, a third resistor coupled between the noninverting input and the second terminal; and a fourth resistor coupled between the noninverting input and the mid voltage. The operational amplifier of the controller may comprise a first network coupled between the inverting input and the output of the differential amplifier comprising a fifth resistor coupled in series with a first capacitor both being coupled in parallel with a sixth resistor, and a second network coupled between the inverting input and the output of the operational amplifier comprising a seventh resistor coupled in series with a second capacitor both being coupled in parallel with a eighth resistor. The device can further comprise a resistor coupled between the inverting input and the noninverting input of the amplifier.

A method of operating a linear lambda probe having four terminals may comprise the steps of:
  determining the difference voltage between a Nernst voltage at the first terminal and a reference voltage;
  feeding the difference voltage to a control circuit for converting it into a pump current;
  feeding the pump current to the second terminal;
  determining the voltage difference caused by the pump current at the third and fourth terminal.

The step of determining the difference voltage can use an operational amplifier. The control circuit can be an integral-action controller, a proportional-plus-derivative controller, or a proportional-plus-integral-plus-derivative controller. The method can further comprise the step of generating a mid voltage for generating the pump current. The most essential feature according to the invention is the displacement of the mid-voltage from the terminal Vp−/Vs− of the probe to its terminal Vp+, as shown in FIG. 2.

BRIEF DESCRIPTION OF THE DRAWINGS

An exemplary embodiment of the invention will be described in more detail below with reference to a schematic drawing, in which:

FIG. 1 shows a basic circuit diagram of a known device, and

FIG. 2 shows a basic circuit diagram of a device according to the invention.

DETAILED DESCRIPTION OF THE PREFERRED EMBODIMENTS

FIG. 1 shows a basic circuit diagram of the known device for operating a linear lambda probe of an internal combustion engine in the region λ=1.

The lambda probe S is composed
a) of what is referred to as the reference cell, i.e. of the electrodes between the measuring chamber and air, represented in the drawing by the Nernst voltage Vs which can be measured between the electrodes, and the internal resistance Ris of the diffusion barrier between them,
b) of what is referred to as the pumping cell, i.e. of the electrodes between the measuring chamber and exhaust gas, represented by the voltage Vp which drops between them and the (reference) resistance Rip between these electrodes, and c) of the calibrating resistor Rc in the probe plug.

The electrodes are applied to the ceramic body of the probe. The ceramic material between the pairs of electrodes is conductive at high temperatures and is used as a solid electrolyte.

As the resistor Rc is subject to considerable environment stresses owing to its installation position in the probe plug, a further resistor Rp is connected in parallel with it in the control unit. This reduces the influence of Rc on the overall precision.

The four terminals Vs+, Vp−/Vs−, Vp+ and Rc have connections leading out of the probe S and are connected to the circuit.

The inverting input of a difference amplifier D is connected to the terminal Vs+ of the sensor S, and its noninverting input is connected to the mid-voltage Vm via a reference voltage Vref. Vm=Vcc/2, Vcc (usually 5 V) being the supply voltage of the circuit.

The inverting input of a pumping current source P, whose noninverting input is connected to the output of the difference amplifier D, is also connected to the mid-voltage Vm.

The output of the pumping current source P is connected to the input Rc of the probe S.

The difference amplifier D compares the Nernst voltage Vs of the probe S (between the external air and measuring cell) with the reference voltage Vref (450 mV) and generates an output voltage which is proportional to the difference and is converted by the pumping current source P into a proportional pumping current Ip which flows through the pumping cell (Rip and Vp) to Vm. The pumping current Ip brings about a change in the oxygen concentration in the measuring cell (not illustrated) of the probe, which in turn results in a change in the Nernst voltage Vs.

The oxygen concentration in the exhaust gas (lambda) is determined by means of a measurement of the pumping current. To do this, the voltage drop which is brought about by the pumping current is measured at the parallel circuit of Rc and Rp by means of a difference amplifier which is not illustrated (cf. IS in FIG. 2).

In this known evaluation circuit, the mid-voltage Vm=Vcc/2 and the reference voltage Vref are connected to the terminal Vp−/Vs− of the lambda probe.

In the stable control state, the Nernst voltage Vs=450 mV and also Vp=450 mV: a state of equilibrium is present between the oxygen flow through the diffusion barrier and the flow of oxygen ions, due to the pumping current Ip.

The maximum range of the output voltage of the pumping current source P extends from approximately 0.1 V to 4.9 V. The disadvantages of this circuit have already been presented above.

A basic circuit of a device according to the invention for operating a linear lambda probe of an internal combustion engine is illustrated in FIG. 2. FIG. 2 shows the lambda probe S which is already described in FIG. 1 and has a circuit according to the invention. An operational amplifier and the parallel circuit of the resistors Rc and Rp which are connected to its inverting input form a pumping current source P. Its noninverting input is supplied with the mid-voltage Vm, and its output is connected to the second probe terminal Vp−/Vs−.

The output of the pumping current source P is connected via the reference voltage Vref and a resistor R3 to the noninverting input of an operational amplifier which is connected to resistors R1 to R4 as difference amplifier D, the inverting input of said operational amplifier being connected via the resistor R1 to the first probe terminal Vs+. The resistor R2 connects the noninverting input to the output, and the resistor R4 leads from the inverting input to the mid-voltage Vm.

The difference amplifier D is followed by a controller R, an operational amplifier which is connected to resistors R5 to R8 and capacitors C1 and C2 as PID controllers, and which can also be embodied as an I controller or PD controller whose noninverting input is supplied with the mid-voltage Vm. The output of this controller R is connected to the fourth probe terminal Rc.

Furthermore, a difference amplifier IS is provided whose inputs are connected to the two terminals of the parallel resistors Rc and Rp.

The difference amplifier D measures the difference between the probe voltage Vs and reference voltage Vref. Its output signal therefore represents the deviation between Vs and Vref—referred to the mid-voltage Vm (error signal of the control loop). The output signal of the difference amplifier D is fed to the controller R which generates a control voltage which is fed to the pumping current source P via the parallel resistors Rc and Rp. The pumping current source P converts this control voltage into a corresponding pumping current which then flows through the pumping cell (Vp, Rip) of the sensor S.

If the voltage at the parallel circuit of Rc and Rp is measured by means of the difference amplifier IS, a very precise and already standardized measure of the pumping current Ip, and thus of $\lambda$, is obtained.

As the input voltage difference of an operational amplifier is very small—it corresponds to the offset voltage and is generally less than 10 mV—the third terminal Vp+ of the probe S is approximately at the potential Vm (2.5 V). The output voltage range of the operational amplifier is limited by the supply voltage Vcc (5 V) and the saturation voltages of the output stage transistors (approximately 0.1 V); in the case of the pumping current source P it therefore extends from approximately 0.1 V to 4.9 V.

This results in a possible voltage excursion of ±2.4 V (2.5 V−0.1 V=+2.4 V; 2.5 V−4.9 V=−2.4 V) for the pumping cell of the probe S (terminals Vp+, Vp−). This is more than sufficient to obtain the maximum permissible or necessary pumping voltage of ±2.0 V with a required pumping current of ±12 mA.

The design of the pumping current source P also ensures that the voltage at the inverting input of the amplifier IS is always at the mid-voltage Vm. As a result, the voltage drop which is to be measured at the parallel resistors Rc/Rp does not have a common mode component. This thus in principle avoids a measuring error caused by the finite common mode suppression of the amplifier P (for example 60 dB). In addition, the input of the difference amplifier IS is always operated in the vicinity of the mid-voltage Vm. In this range, operational amplifiers have the smallest errors (offset, common mode, amplification, linearity, leakage currents, etc.).

Both measures therefore permit a measuring amplifier to be constructed with the smallest possible measuring error, which corresponds to the requirements set.

The advantages of the circuit according to the invention are as follows: the pumping current is then measured with respect to the fixed mid-voltage Vm. The common mode error described above is thus avoided and the precision of the measurement is thereby significantly improved; the measurement of the Nernst voltage Vs (and the sensing of the probe internal resistance Ris, indicated in FIG. 2 as a block with the reference symbol RIM and not explained in more detail) is now admittedly subjected to a common mode signal (Vp=2.5 V±2 V), but these measurement variables are significantly more fault-tolerant (Vs can fluctuate by only up to 50 mV owing to the enormous steepness of the probe characteristic curve. The measurement signal for determining the internal resistance is a high-frequency alternating voltage. The comparatively slow changes in the common mode signal are therefore virtually completely irrelevant); the voltage which is available for the probe is increased by the amount of the voltage drop at the reference resistor Rip. (This can be up to 12 mA*100Ω=1.2 V depending on the probe and the application); during operation with a supply voltage Vcc=5 V, a probe voltage Vp of approximately ±2.5 V can now also be obtained with high pumping currents (Ip=±12 mA). A separate voltage controller is not necessary. This saves costs; the operation of the probe is not restricted even when the battery voltage is low (+6 V).

The invention claimed is:

1. Device for operating a linear lambda probe having a first, second, third, and fourth terminal, comprising:
   a differential amplifier having an inverting input being coupled with the first terminal and a noninverting input being coupled in series with a reference voltage source and the second terminal and having an output;
   a controller having an inverting input coupled with the output of the differential amplifier and a noninverting input receiving a mid voltage and an output;
   a pumping current source having an inverting input coupled with the third terminal and a noninverting input receiving the mid voltage and an output coupled with the second terminal;
   an amplifier having an inverting input coupled with the third terminal and a noninverting input coupled with the fourth terminal and the output of the controller.

2. The device as claimed in claim 1, wherein the reference source is coupled with the mid voltage.

3. The device as claimed in claim 1, wherein the controller is an integral-action controller.

4. The device as claimed in claim 1, wherein the controller is a proportional-plus-derivative controller.

5. The device as claimed in claim 1, wherein the controller is a proportional-plus-integral-plus-derivative controller.

6. The device as claimed in claim 1, wherein the pumping current source and the controller each comprise an operational amplifier.

7. The device as claimed in claim 6, wherein the operational amplifier of the controller comprises a first network coupled between the inverting input and the output of the differential amplifier comprising a fifth resistor coupled in series with a first capacitor both being coupled in parallel with a sixth resistor, and a second network coupled between the inverting input and the output of the operational amplifier comprising a seventh resistor coupled in series with a second capacitor both being coupled in parallel with a eighth resistor.

8. The device as claimed in claim 1, wherein the differential amplifier further comprises a first resistor coupled between the inverting input and the output, a second resistor coupled between the inverting input and the first terminal, a third resistor coupled between the noninverting input and the second terminal; and a fourth resistor coupled between the noninverting input and the mid voltage.

9. The device as claimed in claim 1, further comprising a resistor coupled between the inverting input and the noninverting input of the amplifier.

10. Method of operating a linear lambda probe having four terminals comprising the steps of:
    determining the difference voltage between a Nernst voltage at the first terminal and a reference voltage;
    feeding the difference voltage to a control circuit;
    generating a control voltage from said difference voltage;
    feeding said control voltage to a pump current source via a calibration resistor in said linear lambda probe;
    converting the control voltage into a pump current;
    feeding the pump current to said linear lambda probe through the second terminal; and
    determining the voltage across the calibration resistor within said linear lambda probe at the third and fourth terminal.

11. The method as in claim 10, wherein the step of determining the difference voltage is performed by an operational amplifier.

12. The method as in claim 10, wherein the control circuit is an integral-action controller.

13. The method as in claim 10, wherein the control circuit is a proportional-plus-derivative controller.

14. The method as in claim 10, wherein the control circuit is a proportional-plus-integral-plus-derivative controller.

15. The method as in claim 10, further comprising the step of generating a mid voltage for generating the pump current.

* * * * *